United States Patent [19]

Coll

[11] Patent Number: 5,354,263
[45] Date of Patent: * Oct. 11, 1994

[54] URETERAL STENT-CATHETER HAVING VARYING DIAMETER STENT

[76] Inventor: Milton E. Coll, 6 Pear Tree La., Lafayette Hill, Pa. 19444

[*] Notice: The portion of the term of this patent subsequent to May 26, 2009 has been disclaimed.

[21] Appl. No.: 78,816

[22] Filed: Jun. 21, 1993

Related U.S. Application Data

[63] Continuation-in-part of Ser. No. 885,789, May 20, 1992, Pat. No. 5,221,253, which is a continuation of Ser. No. 704,718, May 20, 1991, Pat. No. 5,116,309, which is a continuation of Ser. No. 301,090, Jan. 25, 1989, abandoned.

[51] Int. Cl.$^5$ .............................................. A61M 37/00
[52] U.S. Cl. .................................... 604/8; 604/164; 604/281
[58] Field of Search ........................ 604/8–10, 604/93, 95, 164, 264, 280, 281; 128/656–658

[56] References Cited

U.S. PATENT DOCUMENTS

| | | | |
|---|---|---|---|
| 3,757,768 | 10/1973 | Kline | 604/95 |
| 4,307,723 | 12/1981 | Finney | 604/281 |
| 4,405,314 | 10/1983 | Cope | 604/164 |
| 4,531,933 | 7/1985 | Norton et al. | 604/8 |
| 4,610,657 | 9/1986 | Densow | 604/8 |
| 4,643,720 | 2/1987 | Lanciano | 604/95 |
| 4,671,795 | 6/1987 | Mulchin | 604/8 |
| 4,713,049 | 12/1987 | Carter | 604/8 |
| 4,787,884 | 11/1988 | Goldberg | 125/657 |
| 4,790,809 | 12/1988 | Kuntz | 128/657 |
| 4,790,810 | 12/1988 | Pugh et al. | 604/8 |
| 4,813,925 | 3/1989 | Anderson, Jr. et al. | 604/8 |
| 4,820,262 | 4/1989 | Finney | 604/8 |
| 4,838,879 | 6/1989 | Tanabe et al. | 128/658 |
| 4,913,683 | 4/1990 | Gregory | 604/8 |
| 4,931,037 | 6/1990 | Wetterman | 604/8 |
| 4,957,479 | 10/1990 | Roemer | 604/8 |

FOREIGN PATENT DOCUMENTS 2577809  8/1986  France .................................... 604/8

*Primary Examiner*—John D. Yasko
*Assistant Examiner*—Anthony Gutowski
*Attorney, Agent, or Firm*—Pennie & Edmonds

[57] ABSTRACT

A tubular flexible stent, a combination of stent-catheter, and method thereof, comprises a flexible tubular drain passage segment and a flexible tubular ureteral catheter receiving segment which is collinearly integral with the passage segment. The stent is formed with a curl at each end of the drain passage segment and the catheter receiving segment. The outer diameter of the catheter receiving segment is larger than that of the drain passage segment, wherein the junction therebetween is gradually tapered to form a continuous, non-abrupt outer surface. The length of the drain passage segment is substantially longer than that of the catheter receiving segment. A rigid ureteral catheter is inserted into the receiving segment to straighten the preformed curl formed therein and a stiffening wire is passed through the catheter and the stent to straighten the curl formed in the drain passage segment. A rigid tube is slid over the catheter and abutted against the free end of the receiving segment to pull the catheter out of the stent.

21 Claims, 2 Drawing Sheets

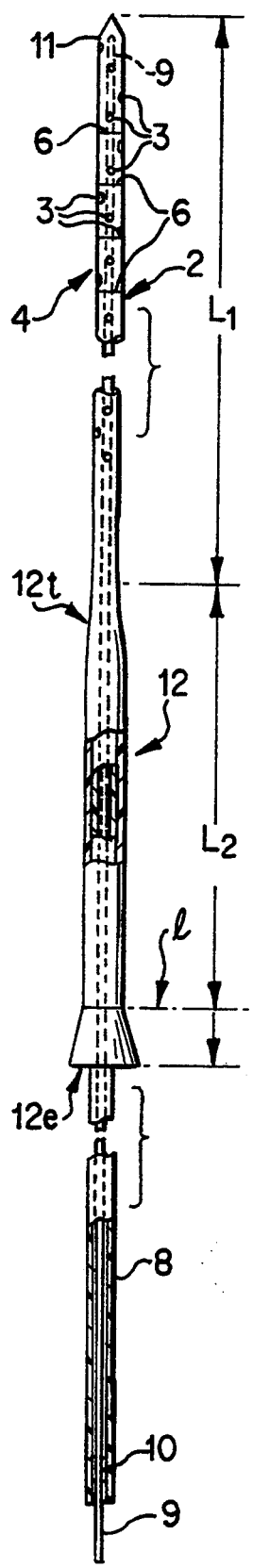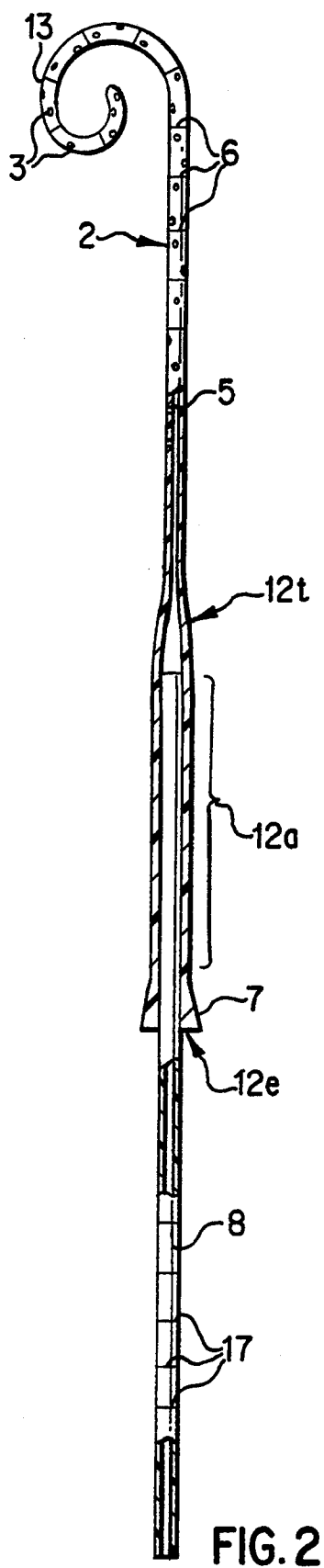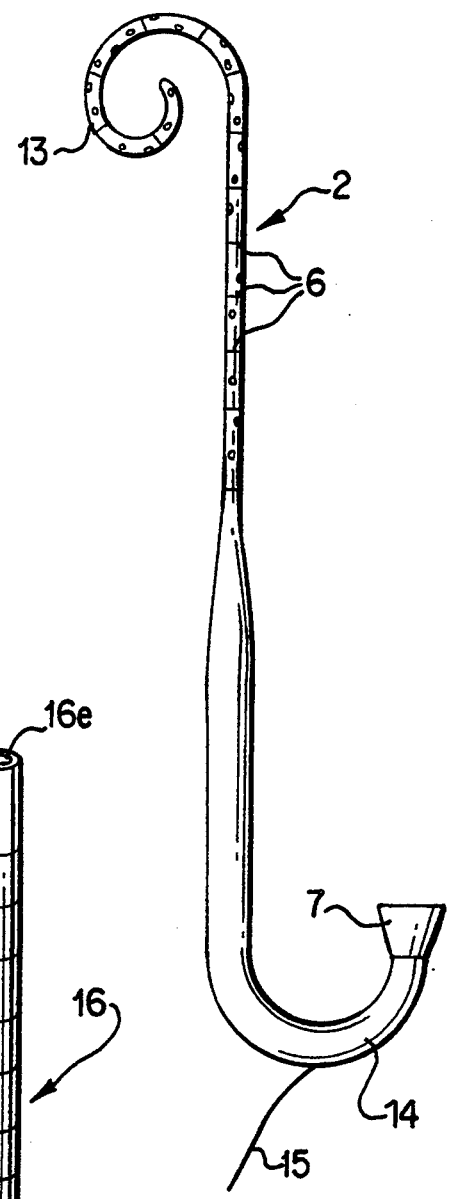
FIG.1  FIG.2  FIG.3  FIG.4

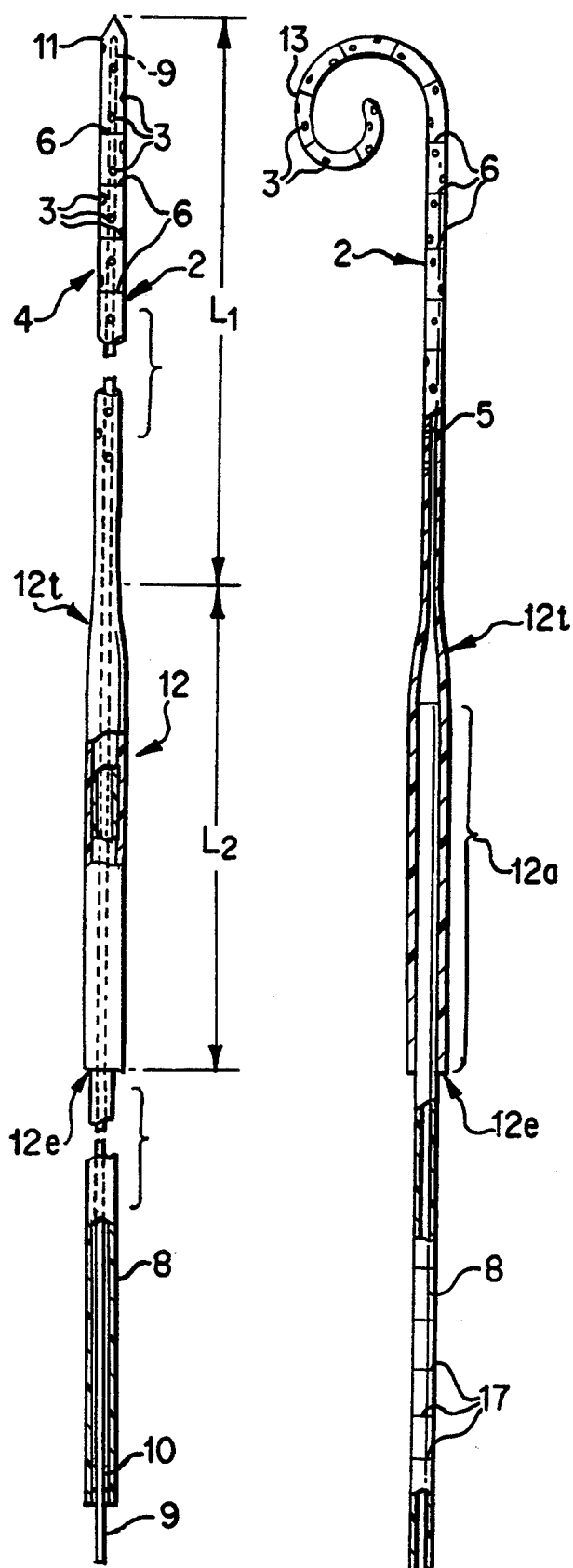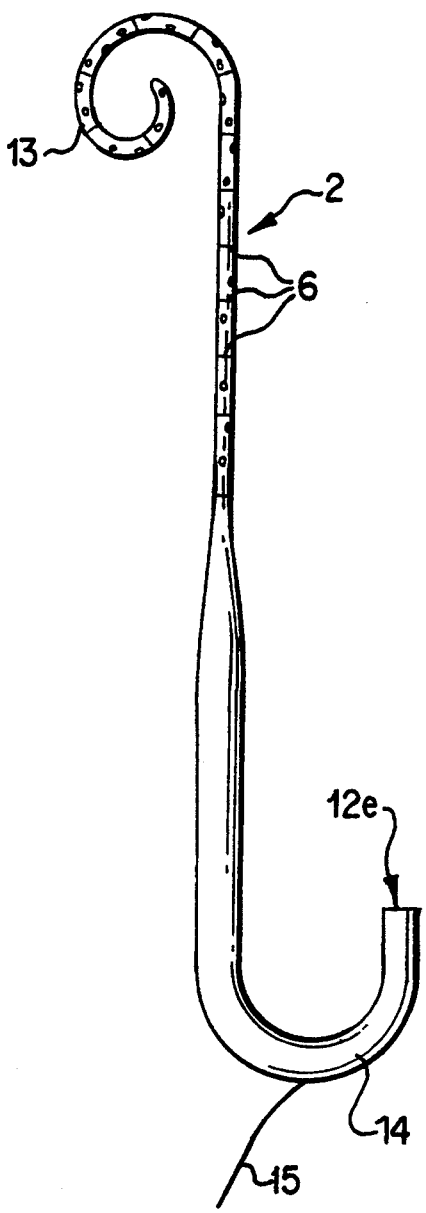
FIG. 5  FIG. 6  FIG. 7

URETERAL STENT-CATHETER HAVING VARYING DIAMETER STENT

CROSS-REFERENCE TO RELATED APPLICATIONS

This is a continuation-in-part of application Ser. No. 07/885,789, filed May 20, 1992, (now U.S. Pat. No. 5,221,253) which is a continuation of application Ser. No. 07/704,718, filed May 20, 1991, now U.S. Pat. No. 5,116,309, which is a continuation of application Ser. No. 07/301,090, filed Jan. 25, 1989, now abandoned. This application is also related to a copending application Ser. No. 08/074,502, filed Jun. 11, 1993, (now pending) which is a continuation of above identified application Ser. No. 07/885,789.

BACKGROUND

Ureteral stents are fundamental to the practice of Urology. These devices allow one to bypass and drain an obstructed ureter, determine urine output from a particular renal unit, and inject contrast to study the upper urinary tract. With the advent of newer methods to manage upper urinary tract stones, such as extracorporeal shock wave lithotropsy (ESWL) disclosed in U.S. Pat. No. 4,913,683 issued to Gregory, and urethroscopy, the use of ureteral stents will continue to grow.

The ideal ureteral stent should allow one to measure urine output from a particular renal unit, drain even tenaciously purulent material, allow injection of contrast for imaging and finally remain indwelling and self contained if longterm ureteral stenting or drainage is required.

The presently available devices consist of external or internal ureteral stents. Both types are usually passed through the ureteral meatus via a cystoscope, though they can be placed openly through different sites in the urinary tract.

Externalized ureteral stents drain the upper urinary tract and pass through the bladder, exiting the urethra and draining into an external collecting device. They allow drainage through ports and a central lumen or channel, and can be irrigated as needed to drain tenacious and obstructing material. By draining externally, the output from the involved renal unit can be carefully monitored. Contrast can be injected as needed to evaluate the upper tract.

Unfortunately, these devices are not self contained and must be secured or they will migrate and be extruded by ureteral peristalsis. They therefore are not suitable for longterm outpatient care.

With this objective in mind, internalized ureteral stents were developed. The most commonly used type is a plastic stent with a curl at both the proximal and distal ends, i.e., a "double-J" stent. The curls are straightened over a central stiffening wire in order to pass the stent, but are reformed when the stiffening wire is removed. The proximal curl prevents distal migration and thereby keeps the device in the renal pelvis. The distal curl is positioned in the bladder to allow completely internalized drainage. No urethral catheter is needed to secure this type of stent, making it ideal for outpatient management.

U.S. Pat. Nos. 4,957,479 issued to Roemet; 4,931,037 to Wetterman; 4,913,683 to Gregory; 4,820,262 and 4,307,723 to Finney 4,790,810 to Pugh, Jr. et al.; 4,790,809 to Kuntz; 4,787,884 to Goldberg; 4,713,049 to Carter; 4,671,795 to Mulchin; and U.S. Pat. No. 4,610,657 to Densaw all show this general approach, while U.S. Pat. Nos. 4,813,925 to Anderson, Jr. et al., and 4,531,933 to Norton et al. show a variation of this concept by using helixes to replace hooks.

The devices shown by these patents, however, have disadvantages. The urine output from the involved renal unit cannot be recorded as only total urethral urine output can be recorded and this would include both kidneys. Also, since the distal end of the stent is internalized, it is not possible to irrigate the tube should it become obstructed. Under these circumstances the obstructed stent could be more detrimental than beneficial as it would occlude an already narrow ureteral lumen. Since the ureteral stent can become obstructed without any external indication, the situation can become dramatically acute before it is realized that the internalized stent is no longer serving its purpose. Lastly, as the stent is not externalized, contrast cannot be injected if needed to image the upper tract.

U.S. Pat. No. 4,913,683 to Gregory allows injection of contrast via a small lumen in the stiffening wire. This lumen, however, is too small to allow reliable and accurate monitoring of urine output or drainage and irrigation of tenacious debris from the involved kidney.

SUMMARY OF THE INVENTION

Accordingly, an object of the present invention is to provide a universal stent which, once in place, functions as an external ureteral stent which can be easily converted into an internalized ureteral stent.

Another object of the present invention to provide a combination catheter-stent that improves on the known prior art devices in that it has the advantages of both an externalized ureteral stent and the advantage of an internalizable ureteral stent once the necessity of externalized drainage or access is overcome.

The above-identified objects and other readily apparent advantages are realized in the present invention by providing a double-J stent with side openings along two-third of its proximal length. The proximal end is preferably closed. The distal one-third of the double-J stent has a wider lumen diameter and is open ended and has consequently a somewhat wider outer diameter than the proximal end. This allows the distal end of the ureteral stent to accept the insertion of a rigid open-ended ureteral catheter. In the above-identified parent applications, the distal end of the double-J stent terminates with a tapered flange having a larger abutting surface in order to allow retraction of the stiff ureteral catheter from the stent against an immobilizing abutting open tube, as seen from FIGS. 1, 2 and 4.

However, the tapered flange is not essential to the present invention, in using with the immobilizing abutting open tube. To provide for an abutting surface in which the immobilizing abutting open tube can abut thereagainst, the inner diameter of the immobilizing abutting open tube and the outer diameter of the catheter is substantially similar, with sufficient clearance to permit the immobilizing abutting open tube to slide relative to the catheter, so that the end of the immobilizing open tube abuts against the distal end of the stent.

The rigid ureteral catheter is long enough to exit the urethra and can be drained by an external drainage system. When the necessity of outside drainage, contrast injection, or monitoring no longer exists, the rigid catheter can be easily disconnected from the flexible ureteral stent. This allows the part of the stent in the bladder to return to its preformed curl to function as a normal double J shaped stent.

BRIEF DESCRIPTION OF THE DRAWINGS

FIG. 1 is a partial fragmentary view of the present ureteral stent in the uncurled form, formed with a tapered flange at the distal end, with the catheter inserted into the distal end of the stent to straighten the curl formed at the distal end and with the stiffening wire inserted through the ureteral catheter and into the proximal end of the stent to straighten the curl formed at the proximal end.

FIG. 2 is a partial fragmentary view of the present ureteral stent of FIG. 1 shown with the stiffening wire removed.

FIG. 3 is a perspective view of the rigid immobilizing abutting open tube or pusher used for removing the rigid ureteral catheter.

FIG. 4 is a perspective view of the present ureteral stent showing the double-J curls formed after detachment of the rigid ureteral catheter and the stiffening wire.

FIG. 5 is a partial fragmentary view of the present ureteral stent in the uncurled form, formed without a tapered flange at the distal end, with the catheter inserted into the distal end of the stent to straighten the curl formed at the distal end and with the stiffening wire inserted through the ureteral catheter and into the proximal end of the stent to straighten the curl formed at the proximal end.

FIG. 6 is a partial fragmentary view of the present ureteral stent of FIG. 5 shown with the stiffening wire removed.

FIG. 7 is a perspective view of the present ureteral stent of FIG. 5 showing the double-J curls formed after detachment of the rigid ureteral catheter and withdrawal of the stiffening wire.

DETAILED DESCRIPTION OF PREFERRED EMBODIMENTS

Two specific embodiments of the present invention are shown in the drawings. For convenience, the same or equivalent elements of the present invention illustrated in the drawings have been identified with same reference numerals. Moreover, the two embodiments are substantially identical, the only difference between the two embodiments being that one embodiment has a tapered flange formed at the distal end and the other does not. However, these two embodiments function substantially identically. Accordingly, the description below will apply equally to both embodiments, except for the difference specifically noted.

Moreover, the embodiments described herein have been contemplated for purposes of illustrating the principles of the present invention. Accordingly, the present invention is not to be limited solely to the exact configuration and construction as illustrated and set forth herein.

In the embodiments shown in the figures, the ureteral stent 1 comprises a flexible plastic tube 2 having apertures 3 along the proximal portion 4, defined by length $L_1$ and a wider catheter receiving segment provided at the distal portion 12, defined by length $L_2$. The apertures 3 communicate between the outside of the stent and the longitudinally extending lumen or channel 5. The lumen 5 extends substantially the entire length of the stent. The stent 1 may be constructed from any plastic material, preferably a soft flexible material provided with conventional length identification or position indicator 6 to indicate the stent's position, i.e, conventional centimeter markings. More preferably, the stent is formed from a radiopaque silicone or silastic material of the type conventionally used for ureteral stents and catheters. Only the proximal portion 4 of the ureteral need be made of radiopaque material but it is preferable that the entire ureteral stent including the flange, if included, be of radiopaque material.

The distal portion 12 has an inside and outside diameter wider than that of the proximal portion 4. The distal portion joins the proximal portion with a gradual taper $12t$ to form a continuous, non-abrupt outer surface. The proximal portion where it joins the distal portion is substantially uniform in diameter. The distal portion 12 includes the gradual taper $12t$ (the length $L_2$ includes the gradual taper portion).

As shown in FIGS. 1, 2 and 4, a tapered flange 7 having a length of about 1 centimeter and with a gradual taper is collinearly and concentrically formed with the free end of the distal portion. FIG. 1 shows the distal portion length $L_2$ including the length of the flange, but the distal portion need not include the length of the flange, as indicated by the dashed line 1. In the embodiment of FIGS. 5-7, the distal end is not formed with any flange, but rather ends in the same diameter as the constant inner and outer diameter portion $12a$ of the distal portion 12.

With respect to the embodiment of FIGS. 1, 2 and 4, the distal end hereafter means the free end or the end $12e$ of the taper (at the largest diameter). With respect to the embodiments of FIGS. 5-7, the distal end means the free end $12e$ of the distal portion 12.

As previously indicated the lumen 5 extends substantially the entire length of the stent with the distal end thereof being opened. A rigid open ended catheter 8 having substantially the same diameter as the constant inner and outer diameter portion $12a$ of the proximal portion of the stent is fitted into the distal end of the stent. The rigid catheter is inserted far enough into the flexible tube to assure secure engagement of the flexible tube. The rigid catheter is held in place by reason of its close or interference fit with the flexible tube.

With respect to the embodiment of FIGS. 1, 2 and 4, the flange 7 functions to allow the pusher or the immobilizing abutting open tube 16 to disengage the rigid ureteral catheter 8 from the stent 1 by abutting against the distal end $12e$ and immobilizing the stent while the rigid ureteral tube is pulled from the stent. The outside flange diameter is larger than the internal diameter of the pusher.

As previously indicated the tapered flange is not essential to the present invention, in using with the pusher 16. To provide for an abutting surface in which the pusher can abut thereagainst, the inner diameter of the pusher and the outer diameter of the catheter 8 is substantially similar, with the inner diameter of the pusher having a sufficient clearance to be able to slide relative to the catheter, so that the end $16e$ of the immobilizing open tube abuts against the distal end $12e$ of the stent. The wall thickness in the distal end $12e$ of the stent should have sufficient area for abutting the pusher.

As shown in FIGS. 1 and 5, a stiffening wire 9 is used to uncurl the curl 13 formed in the proximal portion and to keep the flexible tube stiff while the stent is inserted. The stiffening wire can be passed through a rubber stopper 10 within the distal end of the rigid catheter 8.

The stopper prevents the wire from receding from the distal end of the catheter during insertion. When the stent has been properly placed, the stiffening wire is withdrawn, which will also withdraw the stopper.

Portions adjacent each of the ends 11 and 12 of the stent are formed and set in the shape of gentle curls 13 and 14 as shown in FIGS. 4 and 7. The insertion of the rigid ureteral catheter 8 into the distal end of the stent straightens the curl 14 formed at the distal portion and holds it in straight alignment as shown in FIGS. 2 and 6.

A thread or suture 15 can be attached adjacent to the distal end in order to allow easy removal of the stent by pulling on the suture.

The catheter 8 is formed of material conventionally used for such catheters and stents and is preferably a stiff polymeric material with a hard smooth surface that glides such as polytetrafluorethylene or nylon.

The catheter is marked near its distal end. With the catheter inserted in the distal portion of the stent, the length markings 17 of the catheter can be used in conjunction with the pusher 16 as a visual guide for determining when the pusher 16 abuts against the distal end of the stent. Specifically, prior to the insertion of the stent, when the catheter is fully inserted into the stent, the marking nearest the distal end 12e is noted. Thereafter, the stent-catheter combination are inserted into a ureteral meatus. Since the length of the pusher 16 can be readily measured or is known and the markings 17 can be used to indicate when the pusher abuts against the distal end of the stent prior to pulling out the catheter from the stent.

Different sizes and diameters can be made available with component sizes scaled appropriately. The sizes, lengths and diameters of the various elements are those conventionally used in the art. The precise dimensions of the stent may vary based on the dimensional characteristics of particular patient, as disclosed in U.S. Pat. No. 4,913,683 issued to Gregory, which also disclose a range of sizes of the stent, the disclosure of which is incorporated herein by reference.

As an example of a stent, the proximal portion of the stent may have a 7 French outer diameter (3 French=1 mm), with 4.5-5 French inner diameter (lumen). The constant diameter portion 12a of the distal portion 12 of the stent has a 8.5 French outer diameter with about 7 French inner diameter (lumen). Accordingly, the outer diameter of the taper portion 12t varies in size from 7 to 8.5 French, whereas the lumen of the taper portion varies from 4.5-5 to 7 French. Preferably, the degree of tapering should be less than 10°. More preferably, the degree of tapering should be less than 5°. In the above example, the outer diameter difference of 1.5 French (0.5 mm) between the proximal and distal portions creates the following tapering:

(a) along a length of 0.5 cm, for example, creates gentle tapering of less than 3°;

(b) along a length of 1 cm, for example, creates gentle tapering of less than 2°; and (c) along a length of 2 cm, for example, creates gentle tapering of less than 1°.

With respect to the embodiment having the tapered flange 7, the largest diameter of the tapered flange is 9 French. The taper has a length of about 1 cm and diameter thereof ranges from 9 French to 8.5 French formed at the free end of the distal portion. Accordingly, 0.5 French (=0.167 mm) difference in diameter along 1 cm length creates gentle tapering of substantially less than 1°, which is hardly noticeable. The 0.5 French difference in diameter along 0.5 cm length creates gentle tapering of about 1°. The tapering should not be more than 5°.

In operation, a rigid catheter having about 7 French outer diameter is first inserted into the distal portion of the stent. The outer diameter of the catheter is designed to fit in the lumen of the distal portion, held therein by friction or interference. A conventional stiff guide wire having a diameter of about 0.038 mm is introduced through the catheter and inserted all the way to the end of the distal portion to straighten and stiffen the proximal curl 13. The wire extends further out from the distal part of the catheter and is held in place securely by the detachable rubber stopper 10.

With the wire in place, the proximal curl 13 of the stent is straightened and can be inserted through a 22 French cystoscope, and passed up in the ureteral orifice to the renal cavity. The wire then is removed along with the rubber stopper, allowing the proximal end 11 to curl. The rigid catheter is long enough to extend out through the urethra and the system can be used for an immediate imaging study if needed. To continuously drain the kidney (i.e. to monitor urine output, drain purulent debris, or irrigate to free the system of purulent material) one can secure the rigid ureteral catheter to an indwelling urethral catheter and attach the rigid ureteral catheter to an external drainage bag.

Once the patient is stable and there is no more need for external drainage, the stent can be internalized. The rigid catheter is then completely cleansed with a topical disinfectant and sterile gloves are donned. A sterile pusher 16 having a 8.5 French outer diameter then is lubricated and passed over the rigid ureteral catheter until resistance is met as it abuts the distal end 12e of the stent. The operator will also know that the distal end of the stent has been abutted because the marking on the rigid ureteral catheter can be visualized. Then the rigid catheter is gently pulled through the pusher, holding the pusher in place against the distal end 12e. Then the pusher is then gently extracted from the urethra. The removal of the catheter will allow the distal portion of the stent to form a curl 14 in the bladder and thereby leave a completely internalized stent, as disclosed, for example, in U.S. Pat. No. 4,913,683 to Gregory. The thread or suture can be left attached to the distal end of the stent to allow easy extraction through the urethra.

If desired, the stiffening wire can be inserted first using conventional means. After cutting off the proximal tip of the stent, the stent-ureteral catheter device is passed over the wire in order to insert the catheter combination.

Also if desired, various adapters can be secured to the external end of the rigid ureteral catheter in order to permit irrigation, application of contrast solutions to the renal cavity etc.

The thread or suture is preferably of a synthetic polymer with opaque characteristics. It is attached to the stent at any convenient location.

The advantages of the above described device are many. The materials of construction are conventional. The device can be packaged intact and ready to insert. The various elements can be formed in a variety of sizes, lengths and diameters with component sizes scaled appropriately.

The device obviates the need for separate externalized and internalized ureteral catheters. Further, the device is simple in operation and makes use of concepts and designs proven to be effective and reliable.

It is to be noted that the rigid catheter need only be inserted into the distal portion of the stent to the extend necessary to securely attach to the stent. Accordingly, the rigid catheter does not have to be inserted fully into the distal portion. Further, it can be seen that the specific type of connection described is not critical. Any method of connection that allows the catheter to function as described is contemplated herein. Also, as described, the flange, in connection with the rigid pusher, serves only to hold the stent in place while the stiff catheter is removed. Any other structure that serves to prevent the stent from being pulled out of the renal cavity when the rigid catheter is removed is contemplated.

Given the disclosure of the present invention, one versed in the art would readily appreciate the fact that there can be many modifications of the present invention not specifically depicted and described, but that are well within the scope and spirit of the disclosure set forth herein. Accordingly, all expedient modifications readily attainable by one versed in the art from the disclosure set forth herein that are within the scope and essence of the present invention, are to be included as further embodiments of the present invention.

What is claimed is:

1. A flexible ureteral stent for implantation in a ureteral meatus, comprising:
    a flexible tubular drain passage segment having a plurality of drain passages and a first fluid passage channel extending substantially the entire length of said drain passage segment, said channel communicating with the outside of said drain passage segment, said drain passage segment having a first outer width and said first fluid passage channel having a first channel width, one end of said drain passage segment being closed and a portion of said passage segment forming a preformed curl; and
    a flexible tubular ureteral catheter receiving segment having a second fluid passage channel extending the entire length thereof, said catheter receiving segment being collinearly integral with said passage segment, with said second fluid passage channel also being collinear with said first fluid passage channel, said catheter receiving segment having a second outer width, said second passage channel having a second channel width, said second outer and channel widths being larger than said first outer and channel widths, respectively,
    wherein the junction between said catheter receiving segment and said drain passage segment being gradually tapered to form a continuous, non-abrupt outer surface, a portion of said catheter receiving segment forming another preformed curl, and
    wherein said length of said drain passage segment being substantially longer than said catheter receiving segment.

2. A ureteral stent according to claim 1, wherein the tapering is less than 10°.

3. A ureteral stent according to claim 2, wherein the tapering is less than 5°.

4. A ureteral stent according to claim 1, wherein the length of said drain passage segment is about twice the length of said catheter receiving segment.

5. A ureteral stent according to claim 1, further comprising a tapered flange formed at the free end of said catheter receiving segment.

6. A ureteral stent according to claim 4, wherein the length of said drain passage segment is about twice the length of said catheter receiving segment, including said tapered junction.

7. A ureteral stent according to claim 5, wherein the tapering of said flange is less than 5°.

8. A ureteral stent according to claim 7, wherein the tapering of said flange is less than 1°.

9. A ureteral stent according to claim 1, further comprising a tubular catheter, wherein said curl formed in said catheter receiving segment is straightened by inserting said tubular catheter into said second channel formed in said catheter receiving segment, and whereupon extraction of said tubular catheter, said catheter receiving segment recurls.

10. A ureteral stent according to claim 1, further comprising a stiffening wire, wherein said curl formed in said drain passage segment is straightened by inserting said stiffening wire into said first channel formed in said drain passage segment, and whereupon extraction of said wire, said drain passage segment recurls.

11. A ureteral stent according to claim 1, further comprising a tubular catheter and a stiffening wire, wherein said curl formed in said catheter receiving segment is straightened by inserting said tubular catheter into said second channel formed in said catheter receiving segment and wherein said curl formed in said drain passage segment is straightened by inserting said stiffening wire through said catheter and into said channel formed in said drain passage segment, and whereupon extraction of said wire, said drain passage segment recurls and whereupon extraction of said catheter, said catheter receiving segment recurls.

12. A ureteral stent according to claim 1, wherein at least said drain passage segment of said stent is formed of a radiopaque material.

13. A ureteral stent according to claim 12, wherein said entire stent is formed of a radiopaque material.

14. A ureteral stent-catheter device for implantation in a ureteral meatus, comprising in combination:
    (a) a stent comprising:
    a flexible tubular drain passage segment having a plurality of drain passages and a first fluid passage channel extending substantially the entire length of said drain passage segment, said channel communicating with the outside of said drain passage segment, said drain passage segment having a first outer width and said first fluid passage channel having a first channel width, one end of said drain passage segment being closed and a portion of said passage segment forming a preformed curl; and
    a flexible tubular ureteral catheter receiving segment having a second fluid passage channel extending the entire length thereof, said catheter receiving segment being collinearly integral with said passage segment, with said second fluid passage channel also being collinear with said first fluid passage channel, said catheter receiving segment having a second outer width, said second passage channel having a second channel width, said second outer and channel widths being larger than said first outer and channel widths, respectively,
    wherein the junction between said catheter receiving segment and said drain passage segment being gradually tapered to form a continuous, non-abrupt outer surface, a portion of said catheter receiving segment forming another preformed curl, and
    wherein said length of said drain passage segment being substantially longer than said catheter receiving segment;

(b) a rigid ureteral catheter dimensioned for inserting into said catheter receiving segment of said stent to straighten the preformed curl formed at said catheter receiving segment; and (c) a rigid tube having an inner width sufficient to permit the sliding of said rigid tube over said catheter and abut against the free end of said catheter receiving segment, wherein said rigid tube is used for extracting said catheter from said stent by sliding said tube over said catheter and abutting against said free end and pulling said catheter away from said free end, whereupon on extraction of said catheter from said stent, said catheter receiving segment recurls, both said curls serving to prevent migration of said stent in the ureteral meatus.

15. A ureteral stent-catheter device according to claim 14, further comprising a stiffening wire, wherein said curl formed in said drain passage segment is straightened by inserting said stiffening wire into said first channel formed in said proximal end, and whereupon extraction of said wire, said curl formed in said drain passage segment recurls.

16. A ureteral stent-catheter device according to claim 15, wherein said wire is dimensioned to be inserted through said catheter and into said first channel formed in said drain passage segment.

17. A ureteral stent according to claim 14, wherein the length of said drain passage segment is about twice the length of said catheter receiving segment.

18. A ureteral stent according to claim 14, further comprising a tapered flange formed at the free end of said catheter receiving segment.

19. A ureteral stent according to claim 17, wherein the length of said drain passage segment is about twice the length of said catheter receiving segment, including said tapered junction.

20. A method of inserting an elongated flexible ureteral stent into a renal pelvis comprising the steps of:

inserting a stiff tubular ureteral catheter into a ureteral catheter receiving segment of an elongated flexible ureteral stent having preformed set curls at both ends thereof, said stent having a flexible tubular drain passage segment having a plurality of drain passages and a first fluid passage channel extending substantially the entire length of said drain passage segment, said channel communicating with the outside of said drain passage segment, said drain passage segment having a first outer width and said first fluid passage channel having a first channel width, one end of said drain passage segment being closed and a portion of said passage segment forming one of said preformed curls; and said ureteral catheter receiving segment having a second fluid passage channel extending the entire length thereof, said catheter receiving segment being collinearly integral with said passage segment, with said second fluid passage channel also being collinear with said first fluid passage channel, said catheter receiving segment having a second outer width, said second passage channel having a second channel width, said second outer and channel widths being larger than said first outer and channel widths, respectively, wherein the junction between said catheter receiving segment and said drain passage segment being gradually tapered to form a continuous, non-abrupt outer surface, a portion of said catheter receiving segment forming the other preformed curl, and wherein said length of said drain passage segment being substantially longer than said catheter receiving segment, to straighten the other curl formed in the distal end;

inserting a stiffening wire through said catheter and said stent through said second channel to straighten the curl formed in the drain passage segment of said stent;

inserting the stent-catheter combination through a cystoscope until the proximal end of the stent is within a renal cavity;

withdrawing the stiffening wire from the stent-catheter combination thereby allowing the preformed curl at said proximal end to reform and thus allowing the device to function as an externalized ureteral catheter; and extracting said catheter, allowing the preformed distal curl of the stent to reform to maintain the stent in the renal pelvis.

21. A method according to claim 21, wherein said extracting of said catheter comprises the steps of:

sliding a rigid tube having an inner width sufficient to permit the sliding over said catheter and abut against the free end of said catheter receiving segment;

pulling said catheter away from said free end while immobilizing said stent with said rigid tube, whereupon on extraction of said catheter from said stent, said catheter receiving segment recurls.

* * * * *